United States Patent
Qiu et al.

(10) Patent No.: US 11,490,854 B2
(45) Date of Patent: Nov. 8, 2022

(54) METHOD AND DEVICE FOR ANALYZING WATER CONTENT OF SKIN BY MEANS OF SKIN IMAGE

(71) Applicants: Xianrong Qiu, Beijing (CN); Linlin Xin, Beijing (CN); Limin Zhou, Beijing (CN)

(72) Inventors: Xianrong Qiu, Beijing (CN); Linlin Xin, Beijing (CN); Limin Zhou, Beijing (CN)

(73) Assignee: JINGCHENG WORKSHOP ELECTRONIC INTEGRATION TECHNOLOGY (BEIJING) CO., LTD., Beijing (CN)

( * ) Notice: Subject to any disclaimer, the term of this patent is extended or adjusted under 35 U.S.C. 154(b) by 252 days.

(21) Appl. No.: 16/846,326

(22) Filed: Apr. 11, 2020

(65) Prior Publication Data

US 2020/0237286 A1    Jul. 30, 2020

Related U.S. Application Data

(63) Continuation of application No. PCT/CN2018/110130, filed on Oct. 12, 2018.

(51) Int. Cl.
| | |
|---|---|
| G06K 9/00 | (2022.01) |
| A61B 5/00 | (2006.01) |
| G06T 7/44 | (2017.01) |
| G06T 7/00 | (2017.01) |
| G06V 10/56 | (2022.01) |

(52) U.S. Cl.
CPC ........... *A61B 5/443* (2013.01); *G06T 7/0012* (2013.01); *G06T 7/44* (2017.01); *G06V 10/56* (2022.01); *G06T 2207/30088* (2013.01)

(58) Field of Classification Search
None
See application file for complete search history.

(56) References Cited

U.S. PATENT DOCUMENTS

| 2009/0064268 A1* | 3/2009 | Straub | H04N 21/4384 |
| | | | 725/152 |
| 2014/0092307 A1* | 4/2014 | Fukuda | G06T 5/002 |
| | | | 348/571 |

FOREIGN PATENT DOCUMENTS

| CN | 104299011 A | * | 1/2015 | ......... G06K 9/00234 |
| CN | 104732214 A | * | 6/2015 | |

OTHER PUBLICATIONS

Arimoto, Hidenobu. "Estimation of water content distribution in the skin using dualband polarization imaging." Skin Research and Technology 13.1 (2007): 49-54. (Year: 2007).*

Egawa, Mariko, et al. "Extended range near-infrared imaging of water and oil in facial skin." Applied Spectroscopy 65.8 (2011): 924-930. (Year: 2011).*

* cited by examiner

*Primary Examiner* — Sean M Conner (74) *Attorney, Agent, or Firm* — George Guosheng Wang; Upstream Research and Patent LLC (57) ABSTRACT

The present application discloses a method and a device for analyzing the water content of skin by means of a skin image. The method comprises performing skin feature analysis on an acquired skin image, and obtaining the water content of skin on the basis of the skin features, wherein the skin features comprise a glossiness level and a smoothness level. The present invention clearly shows a reduction in implementation costs when compared to the prior art. The invention also achieves rapid testing.

10 Claims, 6 Drawing Sheets

METHOD AND DEVICE FOR ANALYZING WATER CONTENT OF SKIN BY MEANS OF SKIN IMAGE

BACKGROUND

Technical Field

The present invention relates to a method for analyzing water content of skin by means of skin image, and also to a device for analyzing water content of skin by means of skin image, relates to the field of skin detecting, technology.

Related Art

Using skin detector to measure skin moisture has been widely applied, and has received great attention in skin beauty care and medical applications.

For example, the Chinese Patent with patent number ZL 201310645552.3 discloses a skin moisture detector. It uses multiple electrodes to attach to multiple parts of the human body, and sends tiny current signals to detect the distribution of skin capacitance to obtain skin moisture information in the corresponding area. As another example, the Chinese Patent Application with application number 201510403775.8 discloses a skin parameter measurement circuit and method. It also uses electrodes to contact the skin, measures the skin's capacitive reactance through the moisture detection module, and then detect the skin moisture according to the relationship between the skin's capacitive reactance and the skin moisture.

It can be seen that in the current technology, detectors, electrodes and other technical means are generally used to obtain parameters such as skin capacitance or capacitive reactance, and then the corresponding relationship between capacitance or capacitive reactance and the skin moisture is used to obtain the skin moisture status.

SUMMARY

For disadvantages of the prior art, a primary technical problem to be resolved by the present invention is to provide a method for analyzing water content of skin by means of skin image comprising:

performing skin feature analysis on the skin image, and obtaining water content of the skin according to the skin features.

Preferably, the skin features include glossiness and smoothness.

Preferably, the step of obtaining water content of the skin according to the skin features includes determining the skin to be oily skin if the glossiness is oily; the skin to be dry skin if the glossiness is lack of glossiness.

Preferably, when the glossiness is shiny, the skin is judged as oily skin if the smoothness is large pores with rough texture, the skin is judged as dry skin if the smoothness is relatively rough; the skin is judged as neutral skin if the smoothness is smooth and delicate.

Preferably, the glossiness is judged to be oily, shiny or lack of glossiness, based on an average brightness value, which is acquired according to distribution of brightness values of the skin image processed by SSR algorithm.

Preferably, the glossiness is judged by the following steps:

counting, in the distribution of the brightness values of the skin image, a number of pixels whose brightness value is greater than the average brightness value, and divide the number of the pixels by total number of pixels in the skin image, to acquire a high brightness pixels percentage;

according to preset pixel percentage thresholds M1 and M2, M1 being greater than M2, the skin image with the high brightness pixel percentage greater than M1 being determined to be oily; the skin image with the high brightness pixel percentage less than or equal to M1 and greater than M2 to be shiny, the skin image with the high brightness pixel percentage less than or equal to M2 to be lack of glossiness.

Preferably, further comprising:

calculating brightness values in the skin image that has not been processed by the SSR algorithm to obtain a second brightness average;

according to the second brightness average, count pixels, in the skin image that has not been processed by the SSR algorithm, that have brightness values greater than the second brightness average to obtain the second high brightness pixel point;

calculating a number of the second high brightness pixel points, and calculating a percentage of the second high brightness pixel points in the skin image not processed by the SSR algorithm, to obtain the second high brightness pixel percentage;

adding the second high brightness pixel percentage and the high brightness pixel percentage to obtain a sum of percentages;

comparing the sum of percentages, with the pixel percentage thresholds M1 and M2, so that the skin is judged as oily skin if the sum of the percentages is greater than M1; the skin is judged as shiny if the sum of the percentage is less than or equal to M1 and greater than M2; and the skin is judged as to be lack of glossiness if the sum of the percentages is less than or equal to M2.

Preferably, the smoothness is obtained by calculating a skin roughness and an average pore area.

Preferably, further comprising: Step 32: improving a contrast and a brightness of the skin image by the SSR algorithm;

Step 33: by GLCM (Gray Level Co-occurrence Matrix Method) algorithm, calculating the grayscale difference between pixels in relative directions of horizontal direction, diagonal direction, vertical direction, and against corner direction, to obtain the contrast, and calculating variance of the contrasts in the four directions;

Step 34: classifying roughness according to the variance, based on preset roughness threshold values for classification, and the roughness being classified to rough texture, relatively rough and smooth and delicate.

Preferably, comprising the following steps for calculating the average pore area:

Step 36: performing color space conversion on the skin image processed by the SSR algorithm into HSV color space;

Step 37: calculating a saturation value in the HSV color space, and binarizing the skin image;

Step 38: calculating the pore area and the average pore area: in the binarized image, each black and white border being marked with a circle as a pore; calculating an area of all the circles and a number of the circles, and calculating the average pore area=the area of all the circles/the number of the circles.

Preferably, the skin image is judged to be smooth and delicate if the smoothness is smooth and the average pore area is small pores, the skin image is judged to be relatively rough if the smoothness is relatively rough and the average pore area is normal pores; and the skin image is judged to be large pores with rough texture if the smoothness is rough texture and the average pore area is large pores.

A secondary technical problem to be resolved by the present invention is to provide a device for analyzing water content of skin by means of skin image comprising:

a lens module, for a large shooting range of the skin image, a processor controlling the lens module, being configured to execute program instructions that perform skin feature analysis on the skin image and obtain water content of the skin according to the skin features;

a memory connected to the processor, being used to store the program instructions for the processor.

As compared with the prior art, the present invention of the method and device for analyzing water content of skin by means of skin image may decrease detecting cost and may complete skin detections in a short time. Furthermore, the present invention can directly acquire skin moisture status even on the occasion hard to detect the skin with a skin detection apparatus, and so as to expand the application of the skin moisture analysis.

DETAILED DESCRIPTION

The technical content of the present invention will be described in detail with reference to the accompanying drawings and specific embodiments.

Figure 1:
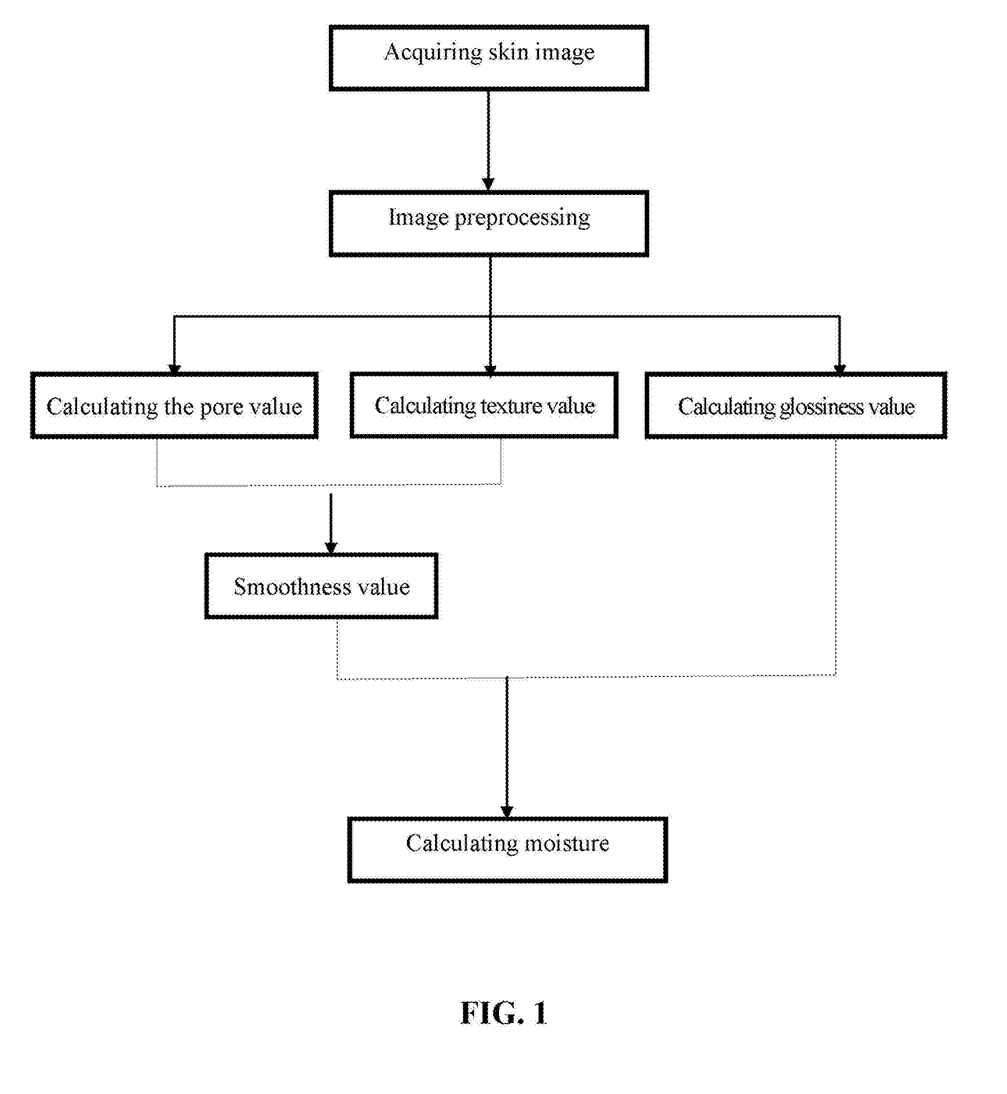
FIG. 1 is a flowchart of the method for analyzing water content of skin by means of skin image in the present invention.

As shown in FIG. 1, in the embodiment of the invention, by analyzing more than 10,000 images of different skin, the corresponding skin characteristics are calculated and analyzed by using the skin images, and then skin characteristics are calculated to analyze the moisture status of the skin. The skin characteristics analyzed include skin glossiness (sheen) and smoothness (roughness). The method specifically includes the following steps:

Step 1: Collect Skin Image

There are many ways to obtain skin image, for instance, the skin image captured by a skin tester. It can be a skin image of the entire face, a skin image of a part of the human face, or a skin image of other parts of the human body.

In this step, low-pass filtering, erosion, and dilation technique can also be performed to remove unnecessary noise and preprocess skin image.

Step 2: Calculate the Glossiness Value

Figure 2:
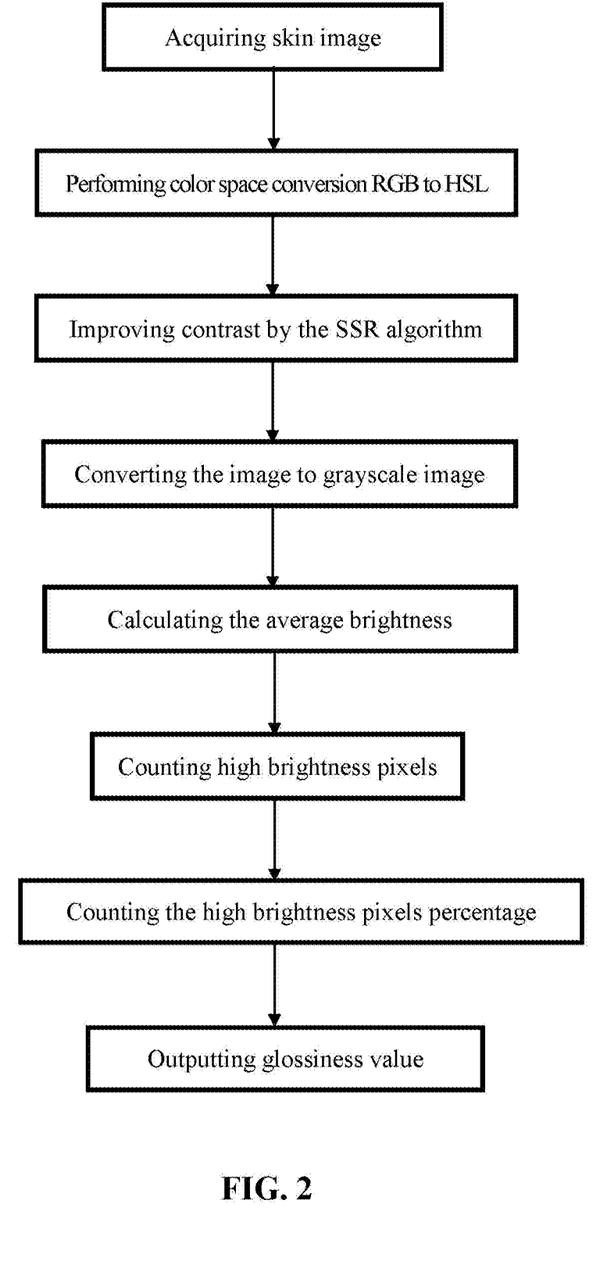
FIG. 2 is a flowchart of the skin glossiness analyzing in FIG. 1.

The invention calculates the glossiness value of the skin image based on the pre-processed skin image, and obtains the classification and result of the glossiness. Glossiness is divided into oily, shine and lack of glossiness. There are many methods for calculating the glossiness value. The calculation method shown in FIG. 2 is adopted in the embodiment of the invention, which will be described in details later with reference to FIGS. 2 to 5.

Step 21: Read Skin Image

The color space of the acquired skin image is converted to HSL color space, where L represents brightness.

Step 22: Improve the contrast and brightness of the image through the SSR algorithm. SSR algorithm can transform image color into color values similar to that recognized by human eyes.

Figure 3:
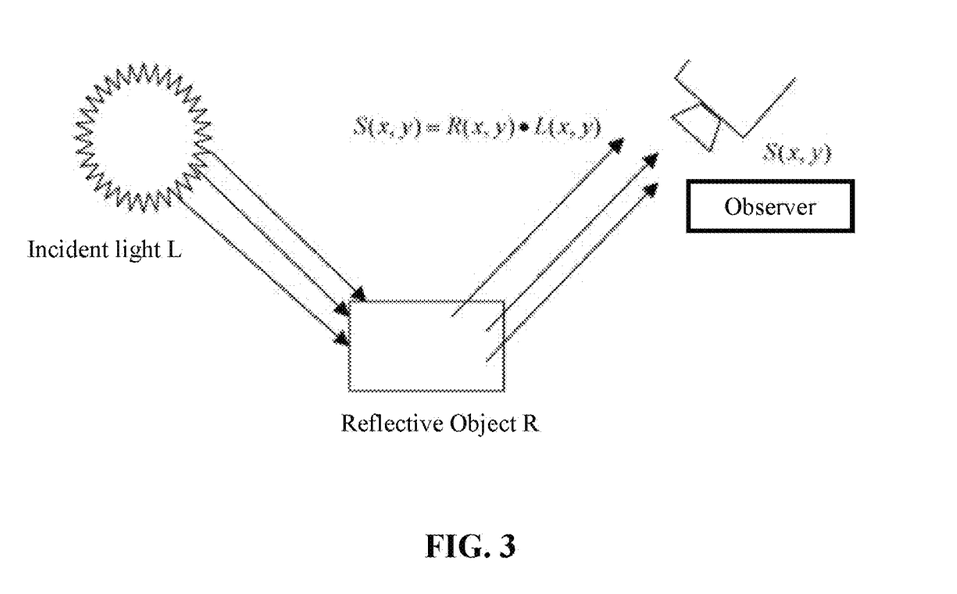
FIG. 3 is a schematical relationship between a reflection image and an incident image in SSR algorithm.
Figure 4:
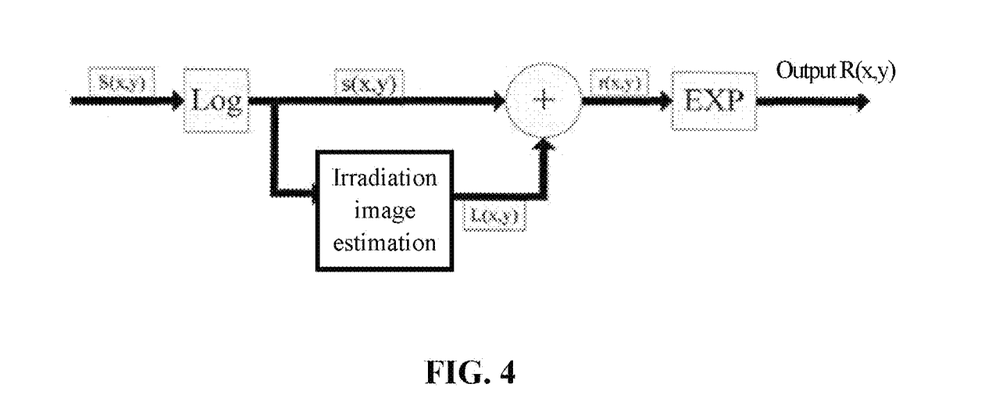
FIG. 4 is a schematical hypothesis of the SSR algorithm.

SSR (Scalable Sample Rate) algorithm is an image enhancement algorithm based on Retinex theory. Based on Retinex theory, an image can be divided into an incident component and a reflection component. For the reflection component, a Gaussian function is used to convolute the component, and then the two components are added to calculate the final result.

Step 23: Perform image preprocessing through low-pass filtering. The preprocessed image S (x, y) outputs the light image L (x, y), and calculate the reflectivity image R (x, y) by the following formula.

$$S(x, y) = R(x, y) \cdot L(x, y)$$

$$r(x, y) = \log R(x, y) = \log \frac{S(x, y)}{L(x, y)}$$

$$r(x, y) = \log S(x, y) - \log[F(x, y) * S(x, y)]$$

$$F(x, y) = \lambda e^{\frac{-(x^2+y^2)}{c^2}}$$

Step 24: Analyze the distribution of brightness value L of the image processed by the algorithm, and obtain the average brightness value.

According to the brightness value L of each pixel in the image processed by the algorithm, the average brightness value can be obtained by simple calculation (it can be arithmetic average or geometric average, etc.).

Step 25: Count the percentage of pixels greater than the average brightness. The number of pixels (high brightness pixels) whose brightness value is greater than the average brightness value L is counted, and is divided by the total number of pixels in the skin image to acquire a high brightness pixels percentage.

Figure 5:
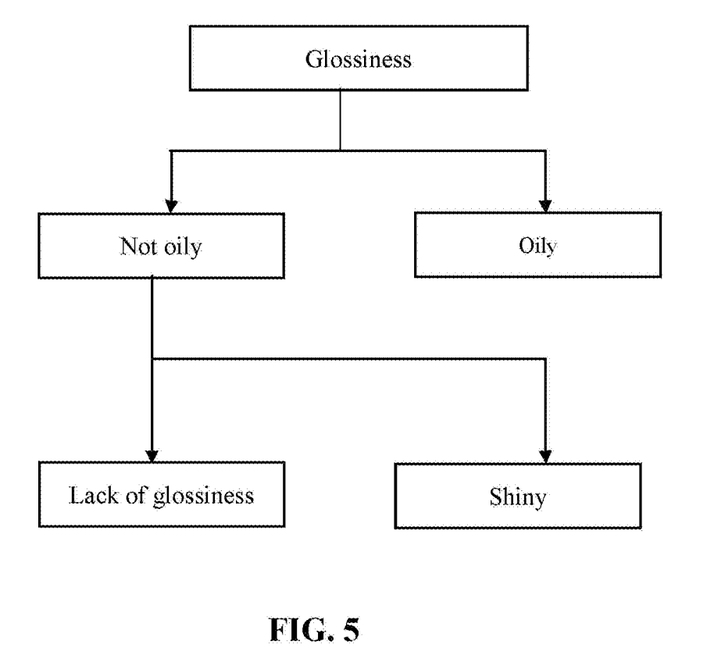
FIG. 5 is schematical glossiness values in FIG. 2.

According to preset pixel percentage thresholds M1 and M2 (M1 is greater than M2), the skin image with the high brightness pixel percentage greater than M1 is determined to be oily, the skin image with the high brightness pixel percentage less than or equal to M1 and greater than M2 is determined to be shiny, the skin image with the high brightness pixels percentage less than or equal to M2 is determined to be lack of glossiness. Among them, M1 and M2 are statistically obtained according to the big data of skin image.

As an optimized solution, it can also be handled as follows:

Calculate the brightness value in the skin image that has not been processed by the algorithm to obtain the second brightness average; according to the second brightness average, count the pixels in the skin image that have not been processed by the algorithm that have a brightness value greater than the second brightness average to obtain the second high brightness pixel point, calculate the number of the second high brightness pixel point, and calculate the percentage of the second high brightness pixel point in the skin image not processed by the SSR algorithm to obtain the second high brightness pixel percentage; The second high brightness pixel percentage and the high brightness pixel percentage are summed to obtain the sum of percentages; according to the sum of percentages, compared with the pixel percentage thresholds M1 and M2, if the sum of the percentages is greater than M1, it is judged as oily, if the sum is less than or equal to M1 and greater than M2, it is interpreted as shiny, if the sum of the percentages is less than or equal to M2, it is determined to be lack of glossiness.

Step 3: Calculate Smoothness Value

Figure 6:
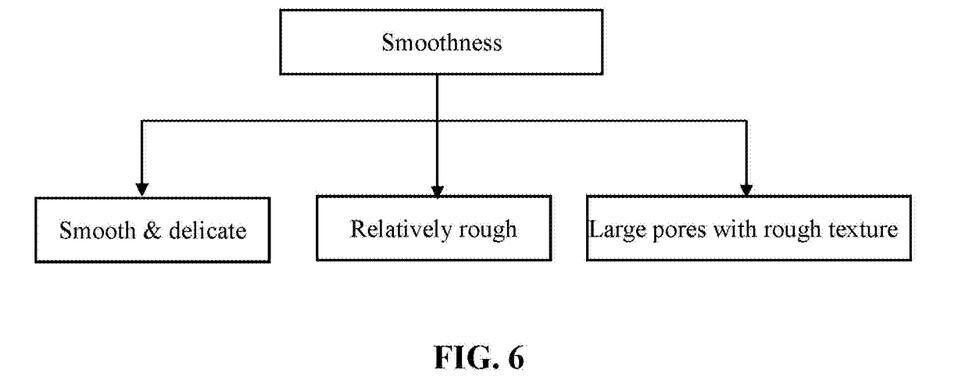
FIG. 6 is schematical smoothness value in FIG. 1.

As shown in FIG. 1, the invention is based on the preprocessed skin image, and the smoothness value is obtained by calculating the skin roughness and pore area in the skin image. FIG. shows the calculation result of the smoothness.

The smoothness value calculation in the invention is obtained based on the pore value and the texture value. Among them, the calculation of pore area and texture value can adopt various calculation methods commonly used in the current technology. For instance:

For the calculation of the texture value, please refer to the applicant's Chinese application number CN201710337597.2 disclosed in the previous patent application using the color space pixel value of the skin image to calculate the absolute deviation mean value. The mean value is used as the method of the roughness characteristic value of the skin image. Or, the roughness extraction method disclosed in the previous Chinese patent application with application number CN201611197869.5 converts the face image from the RGB color space into a YCbCr color space to extract the luminance component, blue chrominance component and red chrominance component map, to find the similarity and roughness of skin color.

For the calculation of pore value, reference can be made to the previous Chinese patent application with application number CN201510554895.8 The patent application discloses a skin pores identification method based on image analysis, which calculates the brightness difference matrix of the pixel area, merges the original image with the brightness difference matrix to obtain a new image, and performing cluster analysis on the new image, iterates the classification to obtain the classified images, counts of the number of skin pores, and calculate the average pixel area of skin pores.

The invention can adopt the calculation method of the above texture value and the pore value, and can also adopt the following calculation method to calculate the roughness and the pore number respectively. Finally, by combining the roughness with the average number of pores, the skin smoothness is divided into smooth and delicate, relatively rough, coarse pores with rough texture.

The steps for calculating the roughness are as follows:

Step 31: Capture skin image

Step 32: Improve the contrast and brightness of skin images through SSR algorithm Step 33: Through GLCM (Gray Level Co-occurrence Matrix Method) algorithm, the relative direction are calculated as 0 degrees (horizontal direction), 45 degrees (diagonal direction), 90 degrees (vertical direction), and 135 degrees (against corner direction) the grayscale difference between pixels to obtain the contrast, and the contrast in the four directions to find the variance.

Because the grayscale of adjacent pixels along the texture direction is essentially the same, and the adjacent pixels in the vertical texture direction have a large grayscale difference, the main diagonal element value is used to determine the texture orientation; The discreteness of the pixel value is used to reflect the thickness of the texture. The pixel value far from the main diagonal is high, that is, the discreteness is large, which means the grayscale difference ratio between adjacent pixels is high, indicating that the texture perpendicular to the direction of the image is fine.

The GLCM algorithm can extract 14 texture features, of which contrast (moment of inertia) can reflect image clarity and texture strength. The larger the contrast value is, the deeper the texture grooves are, and the easier it is to be observed. When the difference between the above four directions is greater, the variance will be greater. Texture often exhibits a single directionality, so in terms of contrast, the more complex the texture, the greater the contrast difference between the four directions. On the contrary, if the skin is smooth, the closer the contrast in four directions is, the smaller the variance will be.

Step 34: Roughness classification according to the contrast variance value. The roughness threshold value for classification is set in advance, and the roughness categories are divided according to the threshold value.

The selection of the roughness threshold value is based on statistics of a large amount of skin data, which is stored in the memory of skin tester in advance. The invention set two roughness threshold values, a first roughness threshold and a second roughness threshold (greater than the first roughness threshold) If the contrast variance value is less than the first roughness threshold value, it is judged as smooth; if the contrast variance value is greater than the second roughness threshold, it is judged as rough texture; if the contrast variance value is greater than or equal to the first roughness threshold value and less than or equal to the second roughness threshold value, it is judged as relatively rough.

In the invention, the steps of calculating the average pore area based on the skin image processed by the SSR algorithm include:

Step 35: Capture the skin mages and perform algorithm processing.

Because Step 35 has the same effect as Step 31 and 32 calculating the roughness, the output result of Step 32 can be directly used to calculate the pore area during the calculation of the roughness in the actual calculation process.

Step 36: Perform the color space conversion on the image processed by the algorithm and convert it into HSV color space.

Step 37: Calculate the saturation value S in the HSV color space.

For the saturation value S, the maximum inter-class variance method (also called the Otsu method) is used to calculate the binarization threshold. And using the threshold to binarize the image, it is divided into two parts: high saturation area and low saturation area. The pores are regarded as gray area relative to the skin and are low saturation areas; the skin is high saturation areas. The larger the pores are, the greater the differences in color saturation are.

The main function of maximum variance between classes is to find out the threshold between the background and the target. Through the distribution of grayscale, the threshold value is found. The pores are the target, and the skin is the background. The larger the inter-class variance between the two regions, the greater the difference between the two regions that make up the image, when the two regions are wrongly divided, the difference between the two regions will become smaller. So the maximum inter-class variance method is used to obtain the segmentation threshold value that maximizes the variance between the two regions, which means that the probability of misdivision between the two regions is the smallest. It can be seen that the calculation results of the pores obtained by the invention is most accurate.

Figure 7:
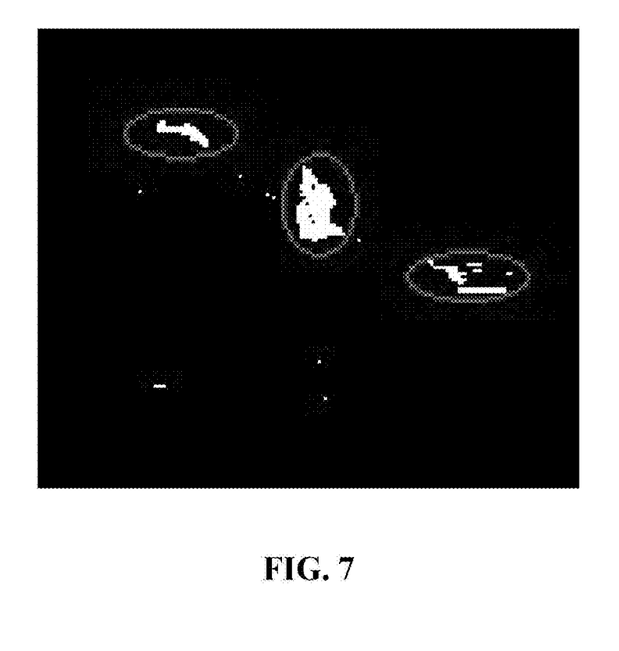
FIG. 7 is schematical black and white borders in a binarized skin image.

The threshold value is found by the method of maximum variance between classes, the threshold value (high saturation, skin) is converted to black, while the threshold value (low saturation, pores) is converted to white to form a black and white image. The black and white border around the pores is created, indicating the boundary between the pores and the surrounding skin.

In addition, those skilled technicians in the industry can comprehend that if the skin image is low-pass filtered, eroded, and expanded to remove unnecessary noise, the pore calculation result in the invention can be more accurate.

Step 38: Calculate pore area and the average pore area

For the binarized image, each black and white border in the image is marked as a circle (as shown in FIG. 7) as a pore. Calculate the area of all circles and the number of circles, and calculate the mean value=area/number of circles as the average pore area.

The threshold value of the pore area is pre-stored in the memory of the skin tester, and the mean value of the pore area is divided into thick pores and normal pores.

Step 39: Division of smoothness

As shown in FIG. 6, according to the roughness classification value and mean value of pore area obtained in the previous steps, the skin image is divided as shown in Table 1 to obtain smooth values.

TABLE 1

Table of smooth values obtained according to the average value of roughness and pore area

| Roughness | Average Pore Area | | |
|---|---|---|---|
| | Large Pores | Normal Pores | Small Pores |
| Smooth | | | Smooth and delicate |
| Relatively rough | | Relatively rough | |
| Rough Texture | Large pores with rough texture | | |

Figure 8:
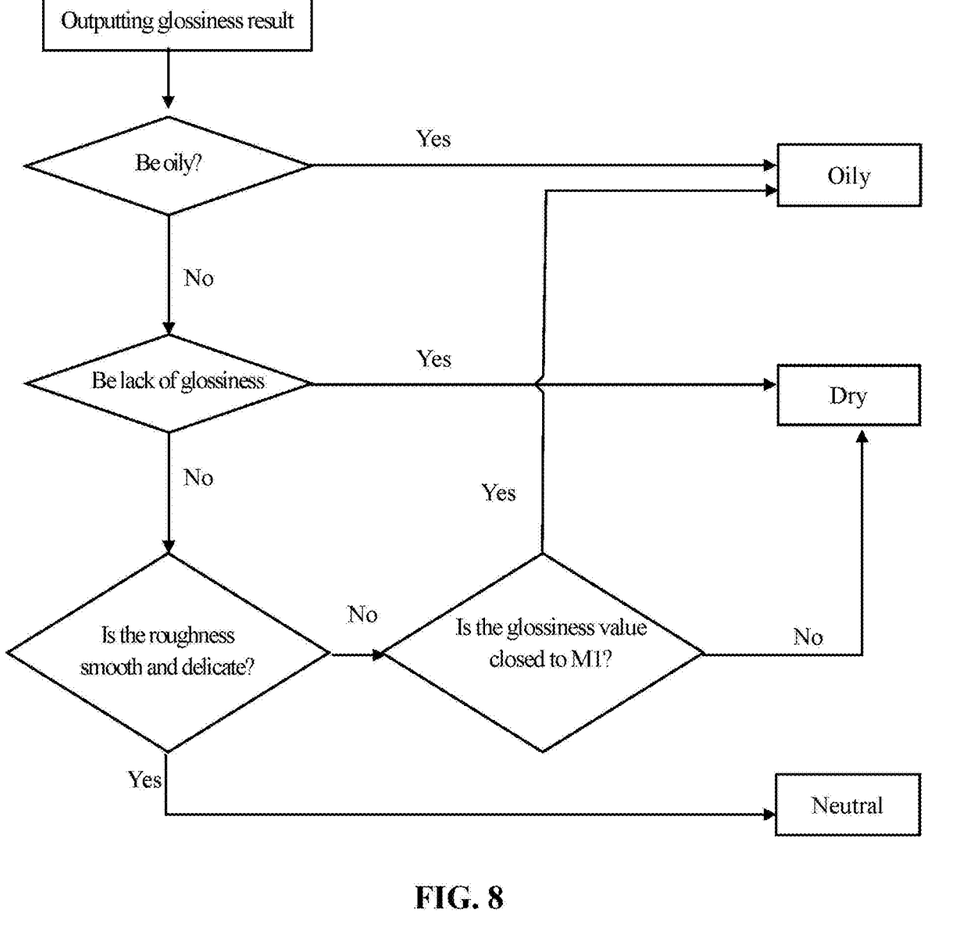
FIG. 8 is a flowchart of the qualitative judgment for skin moisture status in FIG.

Step 4: Combine the Smoothness Value and Glossiness Value to Calculate the Skin Moisture Status The skin moisture status obtained by the invention is calculated based on the smoothness value and glossiness value of the image, rather than directly detected by a sensor as in the current technology. Referring to FIG. 8, in the method for analyzing skin moisture using skin images provided by the invention, the qualitative judgment steps for skin moisture status are as follows:

Step 41: According to the glossiness value, determine whether the glossiness output result is oily. If the glossiness is oily, the result of skin moisture can be oily skin; if it is not oily, proceed to the next step;

Step 42: Determine whether the glossiness output result is lack of glossiness. If the glossiness is lack of glossiness, the skin moisture result is dry skin; if it is not lack of glossiness, that is, the skin is shiny, go to the next step;

Step 43: Determine whether the smoothness value is smooth and delicate. If it is smooth and delicate, it means that in this case, the glossiness of the skin is shiny, and the smoothness is smooth and delicate, that is, the result of skin moisture can be obtained as neutral skin; if the smoothness is not smooth and delicate, then go to the next step;

Step 44: Determine whether the glossiness value is close to the oil glossiness value. Close to the oil light value means that when calculating the glossiness value, the percentage of pixels in the skin image greater than the highlight threshold A is less than but close to M1, for instance, the percentage of pixels in the skin image greater than the highlight threshold A is 85% to 99% of M1.

Step 45: If the glossiness value is close to the oil glossiness value, it is judged as oily skin; Otherwise, it is judged as dry skin. By this step, skin with rough or coarse pores and rough textures can be classified as oily skin or dry skin according to whether the glossiness is close to the glossiness value M1.

It can be understood by those skilled personnel in the industry that, in addition to applying the above method to acquire the moisture status based on glossiness and roughness, the following table can also be used to obtain the skin moisture status using a table lookup method

TABLE 2

Judgment Table of moisture status based on roughness and glossiness

| Smoothness | Glossiness | | |
|---|---|---|---|
| | oily | lack of glossiness | shiny |
| Smooth and delicate | Oily skin | Dry skin | Neutral skin |
| Relatively rough | | | Dry skin |
| Large pores with rough texture | | | Oily skin |

The invention uses skin image analysis to obtain the skin moisture status, on the one hand avoiding the dependence on the skin tester; on the other hand, since the roughness, pores and glossiness are considered in multiple dimensions, the accuracy of the analysis result has been experimentally verified.

Figure 9:
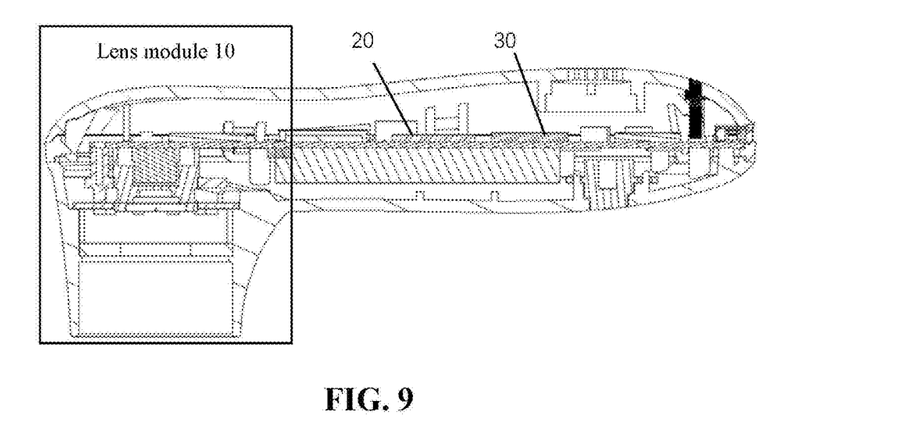
FIG. 9 is schematical device for analyzing water content of skin by means of skin image in the present invention.

The invention also provides a device for acquiring skin moisture status by using skin images (i.e. the skin tester). As shown in FIG. 9, the device is comprised of a lens module 10 with a large shooting range, and a memory 30 connected to the processor 20. Among them, the lens module 10 can achieve a large shooting area, the processor 20 is used to execute programs; the memory 30 is used to store program instructions that can execute various method steps when running on the processor 20, as well as threshold values and moisture status judgment tables (such as Table 2) called when the processor runs the program.

Because the skin image is used to analyze the roughness, pores and moisture status in the invention, if the shooting area is too small, the corresponding skin characteristics cannot be captured into a skin image, thereby losing the possibility of image analysis. Therefore, the shooting area of the lens module in the invention needs to be greater than or equal to 1.5×1.5 cm$^2$ so as to obtain enough skin characteristics.

The method and device for analyzing skin moisture using skin images provided by the invention are described in detail above. For a person of ordinary skill in the art, any apparent change made thereon without departing from the essence of the present invention shall be considered a violation of the patent right of the present invention, and shall bear a corresponding legal responsibility.

What is claimed is:

1. A method for analyzing water content of skin by means of skin image comprising:
    performing skin features analysis on the skin image;
    obtaining water content of the skin according to the skin features, wherein the skin features include glossiness and smoothness, and the glossiness is judged to be oily, shiny or lack of glossiness based on an average brightness value, which is acquired according to distribution of brightness values of the skin image processed by Scalable Sample Rate (SSR) algorithm; and
    determining the skin to be oily skin when the glossiness is oily or the skin to be dry skin when the glossiness is lack of glossiness.

2. The method for analyzing water content of skin by means of skin image of claim 1, wherein when the glossiness is shiny, the skin is judged as oily skin if the smoothness is large pores with rough texture; the skin is judged as dry skin if the smoothness is relatively rough; the skin is judged as neutral skin if the smoothness is smooth and delicate.

3. The method for analyzing water content of skin by means of skin image of claim 1, wherein the glossiness is judged by the following steps:
    counting, in the distribution of the brightness values of the skin image, a number of pixels whose brightness value is greater than the average brightness value, and divide the number of the pixels by total number of pixels in the skin image, to acquire a high brightness pixels percentage;
    according to preset pixel percentage thresholds M1 and M2, M1 being greater than M2, the skin image with the high brightness pixel percentage greater than M1 being determined to be oily; the skin image with the high brightness pixel percentage less than or equal to M1 and greater than M2 to be shiny, the skin image with the high brightness pixel percentage less than or equal to M2 to be lack of glossiness.

4. The method for analyzing water content of skin by means of skin image of claim 3, further comprising:
    calculating brightness values in the skin image that has not been processed by the SSR algorithm to obtain a second brightness average;
    according to the second brightness average, count pixels, in the skin image that has not been processed by the SSR algorithm, that have brightness values greater than the second brightness average to obtain the second high brightness pixel point;
    calculating a number of the second high brightness pixel points, and calculating a percentage of the second high brightness pixel points in the skin image not processed by the SSR algorithm, to obtain the second high brightness pixel percentage;
    adding the second high brightness pixel percentage and the high brightness pixel percentage to obtain a sum of percentages;
    comparing the sum of percentages, with the pixel percentage thresholds M1 and M2, so that the skin is judged as oily skin if the sum of the percentages is greater than M1; the skin is judged as shiny if the sum of the percentage is less than or equal to M1 and greater than M2; and the skin is judged as to be lack of glossiness if the sum of the percentages is less than or equal to M2.

5. The method for analyzing water content of skin by means of skin image of claim 1, wherein the smoothness is obtained by calculating a skin roughness and an average pore area.

6. The method for analyzing water content of skin by means of skin image of claim 5, further comprising:
    Step 32: improving a contrast and a brightness of the skin image by the SSR algorithm;
    Step 33: by Gray Level Co-occurrence Matrix Method (GLCM) algorithm, calculating the grayscale difference between pixels in relative directions of horizontal direction, diagonal direction, vertical direction, and against corner direction, to obtain the contrast, and calculating variance of the contrasts in the four directions;
    Step 34: classifying roughness according to the variance, based on preset roughness threshold values for classification, and the roughness being classified to rough texture, relatively rough and smooth and delicate.

7. The method for analyzing water content of skin by means of skin image of claim 5, comprising the following steps for calculating the average pore area:
    Step 36: performing color space conversion on the skin image processed by the SSR algorithm into HSV color space;
    Step 37: calculating a saturation value in the HSV color space, and binarizing the skin image;
    Step 38: calculating the pore area and the average pore area: in the binarized image, each black and white border being marked with a circle as a pore; calculating an area of all the circles and a number of the circles, and calculating the average pore area=the area of all the circles/the number of the circles.

8. The method for analyzing water content of skin by means of skin image of claim 6, wherein the skin image is judged to be smooth and delicate if the smoothness is smooth and the average pore area is small pores; the skin image is judged to be relatively rough if the smoothness is relatively rough and the average pore area is normal pores; and the skin image is judged to be large pores with rough texture if the smoothness is rough texture and the average pore area is large pores.

9. A device for analyzing water content of skin by means of skin image comprising:
    a lens module, for a large, shooting range of the skin image,
    a processor controlling the lens module, being configured to execute program instructions that perform the method for analyzing water content of skin by means of skin image of claim 1;
    a memory connected to the processor, being used to store the program instructions for the processor.

10. The device for analyzing water content of skin by means of skin image of claim 9, wherein when the glossiness is shiny, the skin is judged as oily skin if the smoothness is large pores with rough texture; the skin is judged as dry skin if the smoothness is relatively rough; the skin is judged as neutral skin if the smoothness is smooth and delicate.

* * * * *